United States Patent
Liu et al.

(10) Patent No.: US 12,201,635 B2
(45) Date of Patent: Jan. 21, 2025

(54) MULTI-TARGET KINASE INHIBITOR, PHARMACEUTICAL COMPOSITION, AND PREPARATION METHOD FOR MULTI-TARGET KINASE INHIBITOR AND USE THEREOF

(71) Applicants: GUANGZHOU LIUSHUN BIOTECHNOLOGY CO., LTD., Guangdong (CN); BEIJING BEIKEHUAXIA BIO-MEDICAL TECHNOLOGY CO., LTD., Beijing (CN)

(72) Inventors: Bing Liu, Guangdong (CN); Jingsi Dai, Guangdong (CN); Yan Wang, Beijing (CN); Xueqi Qian, Guangdong (CN); Junjun Dong, Beijing (CN); Xihong Liu, Guangdong (CN); Lianwu Deng, Guangdong (CN); Shuang Xie, Guangdong (CN); Daping Li, Guangdong (CN); Nengan Chen, Guangdong (CN); Jin Ma, Guangdong (CN)

(73) Assignees: GUANGZHOU LIUSHUN BIOTECHNOLOGY CO., LTD., Guangdong (CN); BEIJING BEIKEHUAXIA BIO-MEDICAL TECHNOLOGY CO., LTD., Beijing (CN)

( * ) Notice: Subject to any disclaimer, the term of this patent is extended or adjusted under 35 U.S.C. 154(b) by 643 days.

(21) Appl. No.: 17/441,618

(22) PCT Filed: Nov. 27, 2019

(86) PCT No.: PCT/CN2019/121231
§ 371 (c)(1),
(2) Date: Sep. 21, 2021

(87) PCT Pub. No.: WO2020/186812
PCT Pub. Date: Sep. 24, 2020

(65) Prior Publication Data
US 2022/0125790 A1 Apr. 28, 2022

(30) Foreign Application Priority Data
Mar. 21, 2019 (CN) .......................... 201910220652.9

(51) Int. Cl.
*A61K 31/517* (2006.01)
*A61P 35/00* (2006.01)

(52) U.S. Cl.
CPC ............ *A61K 31/517* (2013.01); *A61P 35/00* (2018.01)

(58) Field of Classification Search
CPC .............................. A61K 31/517; A61P 35/00
See application file for complete search history.

(56) References Cited

U.S. PATENT DOCUMENTS 7,253,286 B2 * 8/2007 Funahashi ............ A61K 31/517
546/153
2008/0214557 A1 * 9/2008 Ueki .................... A61K 9/2013
514/769

FOREIGN PATENT DOCUMENTS

| CN | 109776432 A | 5/2019 | |
| EP | 0860433 A1 * | 3/2002 | ........... C07D 215/20 |

(Continued)

OTHER PUBLICATIONS

Furuta, T., et al. J. Med. Chem. 2006, 49, 2186-2192. (Year: 2006).*

(Continued)

*Primary Examiner* — Eric Olson
*Assistant Examiner* — Samuel L Galster
(74) *Attorney, Agent, or Firm* — NKL Law; Allen Xue

(57) ABSTRACT

A multi-target kinase inhibitor is shown in formula (I), in which R is selected from formula (a), formula (b), formula (c), formula (d), formula (e) and formula (f). The multi-target kinase inhibitor can effectively inhibit the enzymatic activities of RET, VEGFR3 and PDGFRA, and can effectively treat diseases that are regulated and controlled by multi-target kinases and are related to abnormal signal transduction pathways of the multi-target kinases, including cancers of breast, respiratory tract, brain, reproductive organ, digestive tract, urinary tract, eye, liver, skin, head and/or neck and distant metastatic cancers thereof, and lymphoma, sarcoma, leukemia and the like. The active ingredients of the pharmaceutical composition of the present invention comprise a multi-target kinase inhibitor, which accounts for 1-50 wt % of the composition.

(Continued)

-continued (c)

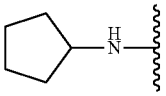

(d)

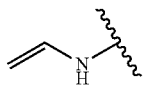

(e)

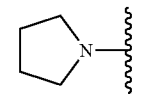

(f)

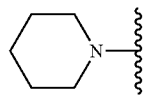

12 Claims, 2 Drawing Sheets

(56) References Cited

FOREIGN PATENT DOCUMENTS

| | | |
|---|---|---|
| EP | 1243582 A1 | 9/2002 |
| WO | 2018145621 A1 | 8/2018 |

OTHER PUBLICATIONS

Garofalo, A., et al. Bioorg. Med. Chem. Lett. 21, 2011, 2106-2112. (Year: 2011).*
Healy, A. M., et al. Advanced Drug Delivery Reviews, 117, 2017, 25-46. (Year: 2017).*
Si, J., et al. WO 2018/145621A1. English Translation. (Year: 2018).*
Xie, Z., et al. J. Med. Chem. 2021, 64, 1283-1345. (Year: 2021).*
Ravez, Severine et al. Synthesis and biological evaluation of di-aryl urea derivatives as c-Kit inhibitors, Bioorganic & Medicinal Chemistry, vol. 23, No. 22, Oct. 24, 2015, ISSN: 0968-0896, pp. 7340-7347.

* cited by examiner

MULTI-TARGET KINASE INHIBITOR, PHARMACEUTICAL COMPOSITION, AND PREPARATION METHOD FOR MULTI-TARGET KINASE INHIBITOR AND USE THEREOF

TECHNICAL FIELD

The present invention relates to the technical field of biomedicine, and in particular to a multi-target kinase inhibitor, a pharmaceutical composition comprising the same, and further a preparation method for the multi-target kinase inhibitor and use thereof.

BACKGROUND

Cells contain complex signal transduction pathways. The signal pathways mediated by tyrosine protein kinase involve changes in a plurality of protein structures and functions of the human body, and abnormal signal transduction of cells is one of key factors in the development and progression of tumors. The tyrosine protein kinase target is the main focus in the research of anti-tumor drugs in recent decades. With the further research and the clinical application of drugs, it is found that the treatment implemented by using single-target drugs to block the specific signal transduction pathways of tumor cells may not be objective enough in efficacy, can cause drug resistance with activated bypass compensation signaling pathways, and has certain toxic and side effects. Therefore, the development of novel multi-target drugs that are free from toxic and side effects and can act upon multiple signaling pathways is of great social significance and has a wide market prospect. RET proteins belong to one of receptor kinases of the cadherin superfamily and have a typical TK structure. RET proteins are receptors for GDNF, and its function is to activate kinase domains through the formation of GDNF-GFRas-Ret, leading to autophosphorylation of intracellular domains and thus initiating multiple signaling pathways to regulate proliferation and differentiation of neural crest cells. The kinases of RET proteins can activate multiple downstream signaling pathways, including an RAS/RAF/ERK pathway, a PI3K/Akt pathway and a JNK pathway. It has been reported that pathogenic mutations, such as gene mutations or rearrangements, in the RET gene will encode RET proteins with abnormal activity, which will transmit abnormally signals and cause multiple effects, including cell growth, survival, invasion, metastasis, etc. Sustained signaling can cause excessive proliferation of cells, leading to development and progression of tumors. The distant metastasis of tumors is one of their important biological characteristics and is also a main reason for the difficulty of radical cure. The expression of VEGF and VEGFR is closely related to the growth, infiltration and metastasis of tumors. The VEGFR family receptors comprise VEGFR-1, VEGFR-2 and VEGFR-3. Research results show that VEGF-C and VEGFR 3 in various tumors can induce the proliferation and migration of endothelial cells, regulate angiogenesis and lymphangiogenesis, and play an important role in regulating the growth and metastasis of tumors. Inhibition of lymphangiogenesis and its regulation mechanism, promotion of tumor metastasis due to lymphangiogenesis and the like have become an important topic in the field of malignant tumor treatment. There are research results showing that VEGF-C can promote tumor-related lymphangiogenesis, and the VEGFR-3 fusion protein can be used to inhibit lymphangiogenesis, suggesting that blocking the VEGFR-3 signaling pathway may be one of the ways of inhibiting lymphatic metastasis of tumors. In addition, when over-expressed VEGFR-3 fusion protein was applied to the human lung cancer cell line LNM35, it was found that it can inhibit lymphangiogenesis and lymphatic metastasis of tumors, and the original lymphatic vessels were not affected by the VEGFR-3 fusion protein.

PDGFRA, as one of the platelet-derived growth factor receptors, is a member of tyrosine protein kinase family. It can promote chemotactic division and proliferation of cells, and plays a very important role in the processes of growth and development, wound repair and the like of organisms. Its over-activation and abnormal expression may induce angiogenesis of tumors, which directly or indirectly promotes the proliferation and migration of tumor cells.

DESCRIPTION OF THE INVENTION

Aiming at overcoming the disadvantages in the prior art, the present invention provides a multi-target kinase inhibitor that can effectively inhibit the enzymatic activities of RET, VEGFR3 and PDGFRA, and can also effectively treat cancers.

Another object of the present invention is to provide a method for preparing the multi-target kinase inhibitor.

Another object of the present invention is to provide use of the multi-target kinase inhibitor.

Still another object of the present invention is to provide a pharmaceutical composition comprising the multi-target kinase inhibitor as an active ingredient.

In order to achieve the above objects, the present invention provides the following technical solutions:

In a first aspect, the present invention provides a multi-target kinase inhibitor, which has a structure shown in general formula (I):

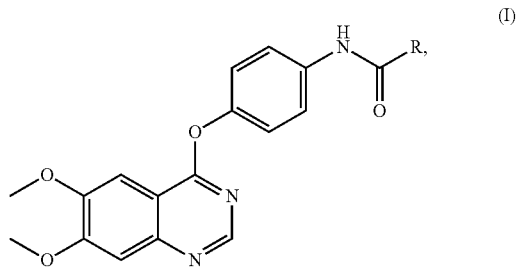

wherein R is selected from the following formula (a), formula (b), formula (c), formula (d), formula (e) and formula (f):

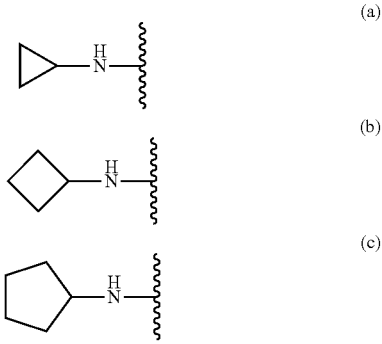

The multi-target kinase inhibitor of the present invention has very good inhibitory activity against RET, VEGFR and PDGFRA, and has a better tumor inhibition effect on a plurality of tumors of mice than positive drugs sorafenib and cabozantinib. Besides, it has the characteristics of no toxic or side effect on heart and better tolerance.

The multi-target inhibitor of the present invention can effectively treat diseases related to abnormal signal transduction pathways of RET, VEGFR and PDGFRA.

In a second aspect, the present invention provides a method for preparing the above multi-target kinase inhibitor, which comprises the following steps:
(1) reacting a compound of formula (II) with a compound of formula (III) to prepare a compound of formula (IV);
(2) reacting a compound of formula (IV) with a compound of formula (V) to prepare a compound of formula (VI); and
(3) reacting a compound of formula (VI) with a compound of formula (VII) to prepare the multi-target kinase inhibitor;

the structural formulas of formula (II), formula (III), formula (IV), formula (V), formula (VI) and formula (VII) being shown as follows:

wherein R is selected from formula (a), formula (b), formula (c), formula (d), formula (e) and formula (f).

In a third aspect, the present invention provides use of the multi-target kinase inhibitor or a pharmaceutically acceptable salt or hydrate thereof in preparing a drug for treating diseases with abnormal transduction of multi-target kinase signaling pathways.

The multi-target kinase signaling pathways are mediated by RET or VEGFR3 or PDGFRA. The multi-target kinase inhibitor can effectively inhibit the enzymatic activities of RET, VEGFR3 and PDGFRA, thereby treating diseases with abnormal transduction of multi-target kinase signaling pathways. The multi-target kinase inhibitor has a good effect on treating occurrence, development and metastasis of tumors.

As a preferred embodiment of the use of the present invention, the diseases with abnormal transduction of multi-target kinase signaling pathways are cancers.

As a preferred embodiment of the use of the present invention, the cancers are at least one of liver cancer, breast cancer, respiratory tract cancer, digestive system tumor, brain cancer, reproductive organ cancer, urinary tract tumor, skin cancer, head and neck cancer, ocular tumor and distant metastatic cancers thereof, and sarcoma, lymphoma and leukemia.

Preferably, the liver cancer includes, but is not limited to, hepatoblastoma, hepatic lymphoma, hepatic mesenchymal tumor, hepatic secondary tumor, gallbladder and extrahepatic bile duct cancer, cholangiocarcinoma, hepatoblastoma, and combined hepatocellular carcinoma; the breast cancer includes, but is not limited to, non-invasive carcinoma, early invasive carcinoma, invasive carcinoma of specific type, and invasive carcinoma of no specific type; the respiratory tract cancer includes, but is not limited to, small cell lung cancer, non-small cell lung cancer, lymphoma, head and neck cancer, and pleural mesothelioma; the digestive system tumor includes, but is not limited to, esophageal tumor, stomach tumor, small bowel tumor, appendiceal tumor, colon and rectal tumor, anal canal tumor, liver and inner bile duct tumor, gallbladder and extrahepatic bile duct tumor, and exocrine pancreatic tumor; the brain cancer includes, but is not limited to, central nervous tumor, peripheral nervous tumor, meninges tumor, and pineal tumor; the reproductive organ cancer includes male reproductive organ tumors including but not limited to prostate tumor, testicular and surrounding tissue tumor, and penile tumor, or female reproductive organ tumors including but not limited to ovarian and peritoneal tumor, fallopian tube and uterine ligament tumor, uterine tumor, cervical tumor, and vulvar tumor; the urinary tract tumor includes, but is not limited to, kidney tumor, invasive urothelial cancer, bladder cancer, villous adenocarcinoma, granulocytic tumor, and umbilical duct cancer; the skin cancer includes, but is not limited to, epithelial cell tumor, melanocytic tumor, lymphohematopoietic tumor, and skin soft tissue tumor; the head and neck cancer includes, but is not limited to, nasal cavity/sinus tumor, laryngopharynx and cervical esophageal tumor, thyroid tumor, and oropharynx/nasopharynx tumor; the ocular tumor includes, but is not limited to, retinoblastoma, eyelid sebaceous gland carcinoma, orbital lymphatic tumor, orbital osteosarcoma, iris melanoma, optic glioma, and iris leiomyoma; the sarcoma includes, but is not limited to, typical osteosarcoma, telangiectatic osteosarcoma, undifferentiated polymorphic sarcoma, gastrointestinal stromal tumor, liposarcoma, and leiomyosarcoma; the lymphoma includes, but is not limited to, hodgkin's lymphoma, B cell lymphoma, T cell lymphoma, and NK cell lymphoma; the leukemia includes, but is not limited to, myeloid myelomonocytic leukemia, monocytic leukemia, erythroleukemia, megakaryocytic leukemia, and lymphoid T and B cell leukemias.

As a preferred embodiment of the use of the present invention, the pharmaceutically acceptable salt is a salt formed from a multi-target kinase inhibitor and an acid; preferably, the acid is methanesulfonic acid, hydrochloric acid, acetic acid, trifluoroacetic acid, tartaric acid, malic acid, citric acid, hydrobromic acid, phosphoric acid, sulfuric acid, trifluoromethanesulfonic acid, benzenesulfonic acid, p-toluenesulfonic acid, 1-naphthalenesulfonic acid, 2-naphthalenesulfonic acid, lactic acid, oxalic acid, succinic acid, fumaric acid, maleic acid, salicylic acid, benzoic acid, phenylacetic acid or mandelic acid; more preferably, the acid is methanesulfonic acid, hydrochloric acid or benzenesulfonic acid.

In a fourth aspect, the present invention provides a pharmaceutical composition comprising the multi-target kinase inhibitor as an active ingredient.

As a preferred embodiment of the pharmaceutical composition of the present invention, the pharmaceutical composition further comprises at least one pharmaceutical excipient known in the pharmaceutical art, wherein the pharmaceutical excipient includes a filler, a binder, a disintegrant, and a lubricating glidant.

As a preferred embodiment of the pharmaceutical composition of the present invention, the multi-target kinase inhibitor accounts for 1-50 wt % of the pharmaceutical composition.

As a preferred embodiment of the pharmaceutical composition of the present invention, the pharmaceutical excipient includes 10-80 w % of a filler, 1-45 wt % of a binder, 5-20 wt % of a disintegrant and 0.1-10 wt % of a lubricating glidant, based on the pharmaceutical composition. Preferably, the filler is an excipient with good stability, fluidity and compressibility, and is selected from at least one of lactose, microcrystalline cellulose, mannitol, sorbitol, calcium hydrogen phosphate, starch, pregelatinized starch, chitosan, sucrose, starch hydrolyzed oligosaccharide, and silicified microcrystalline cellulose; more preferably, the filler is one or more of lactose, microcrystalline cellulose, mannitol, and sucrose.

Preferably, the binder is a polymer with high viscosity, and is selected from at least one of hydroxypropylmethylcellulose, dextrin, carbomer, xanthan gum, gum arabic, sodium alginate, tragacanth, maltodextrin, polyvinylpyrrolidone, and hydroxypropyl cellulose; more preferably, the binder is one or more of polyvinylpyrrolidone, hydroxypropyl methylcellulose, and tragacanth.

Preferably, the disintegrant is an excipient with good fluidity and compressibility, and is selected from at least one of low-substituted hydroxypropyl cellulose, crospovidone, sodium croscarmellose, cross-linked sodium carboxymethyl starch, and sodium carboxymethyl starch; more preferably, the disintegrant is one or more of low-substituted hydroxypropyl cellulose, crospovidone, and sodium croscarmellose.

Preferably, the lubricating glidant is selected from at least one of magnesium stearate, calcium stearate, stearic acid, sodium fumarate, sodium dodecyl sulfate, glyceryl behenate, talc, silica, polyethylene glycol, and sodium stearyl fumarate; more preferably, the lubricating glidant is one or more of magnesium stearate, silica, sodium dodecyl sulfate, and polyethylene glycol.

The pharmaceutical composition provided herein can be prepared in any pharmaceutically acceptable dosage form.

As a preferred embodiment of the pharmaceutical composition of the present invention, the dosage form is an oral solid preparation.

Preferably, the oral solid preparation includes tablets, capsules and granules.

The pharmaceutical composition of the present invention is used for treating patients with middle-stage and terminal esophageal cancer and gastric cancer; 5-250 mg of the pharmaceutical composition preparation is administrated once a day for treating patients with middle-stage and terminal esophageal cancer and gastric cancer; preferably, 10-50 mg of the pharmaceutical combination preparation is administrated once a day for treating patients with middle-stage and terminal esophageal and gastric cancer.

Compared with the prior art, the present invention has the following beneficial effects:

(1) the multi-target kinase inhibitor provided herein can effectively inhibit the enzymatic activities of RET, VEGFR3 and PDGFRA, and can effectively treat diseases that are regulated and controlled by multi-target kinases and are related to abnormal signal transduction pathways of the multi-target kinases, including cancers of breast, respiratory tract, brain, reproductive organ, digestive tract, urinary tract, eye, liver, skin, head and/or neck and distant metastatic cancers thereof, as well as lymphoma, sarcoma and leukemia;

(2) in the preparation of the pharmaceutical composition comprising the multi-target kinase inhibitor of the present invention, the starting materials are pre-treated by ultra-micronization, and a conventional dosage form is adopted, and thus a drug with a smaller particle size is obtained, so that the drug is better dissolved in the body, thereby improving the dissolution and absorption of the drug in the body;

(3) the pharmaceutical composition of the present invention dissolves quickly when prepared into tablets, and the drug release can substantially reach a plateau within 15 min, which is more favorable for absorption of the drug by the upper half part of the small intestine. According to the content of the multi-target kinase inhibitor contained in the pharmaceutical composition as an active ingredient, the pharmaceutical composition only needs to be orally taken once a day by a patient, which greatly improves the compliance of the patient; and (4) in the process of preparing the pharmaceutical composition of the present invention, less organic solvent in the excipients is used, which is beneficial to the environmental protection.

DETAILED DESCRIPTION

Figure 1:
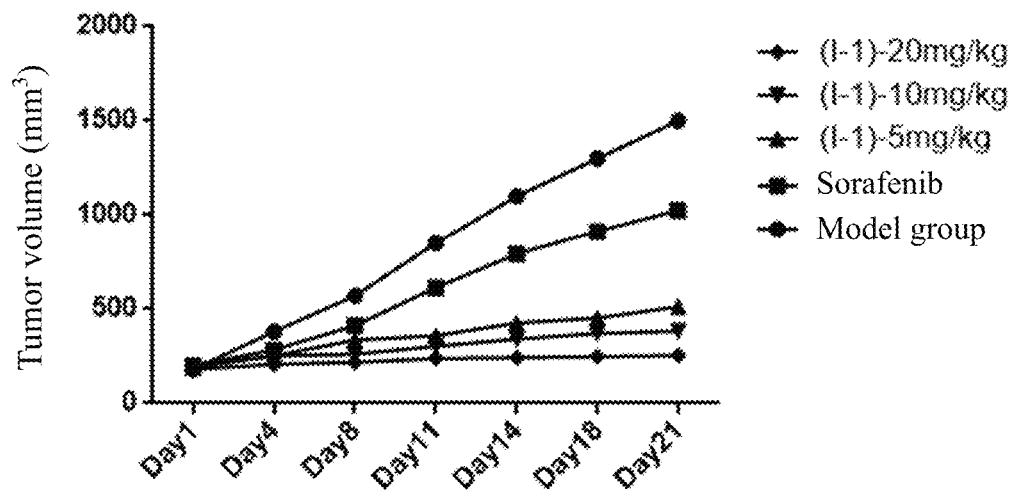
FIG. 1 shows the inhibition of tumor volumes in mice with SMMC-7721 hepatoma by the multi-target kinase inhibitor [Compound (I-1)] of the present invention, wherein formula (I-1) represents Compound (I-1) of the multi-target kinase inhibitor of the present invention.

In order to make the objects, technical solution and advantages of the present invention more apparent, the present invention is further described in detail with reference to specific embodiments.

Example 1

This example is directed to the multi-target kinase inhibitors (I-1), (I-2), (I-3), (I-4), (I-5), and (I-6) of the present invention and methods for preparing the same, wherein the general structural formula of the multi-target kinase inhibitors is shown in formula (I):

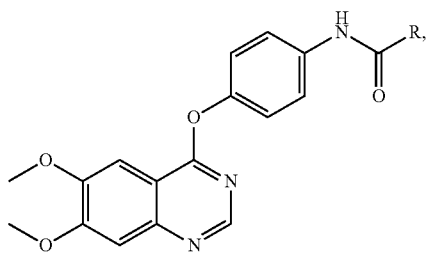

(I)

wherein R is selected from the following formula (a), formula (b), formula (c), formula (d), formula (e) and formula (f):

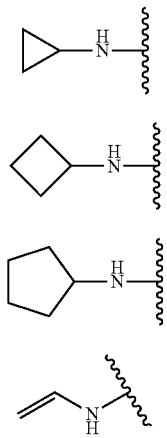

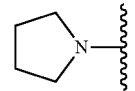

(e)

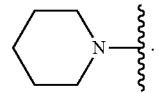

(f)

The method for preparing the multi-target kinase inhibitor comprises the following steps.

(1) Preparation of compound 4-((6,7-dimethoxyquinazolin-4-yl)oxy)aniline [Compound (IV)] 4-aminophenol [Compound (III)] (3.46 g, 31.2 mmol), NaOH (1.26 g, 31.2 mmol) and 50 mL of dimethyl sulfoxide were added into a 250 mL three-neck flask, mixed and stirred. 50 mL of dimethyl sulfoxide was mixed with 4-chloro-6,7-dimethoxyquinazoline [Compound (II)] (5 g, 22.3 mmol), and added into the above reaction solution. After the dropwise addition, the reaction solution was heated to 120° C. and reacted for 2 h. Then the reaction mixture was cooled to 15-20° C., and poured into 100 mL of ice water. When the temperature was controlled to be 15-30° C., the resultant mixture was added with 20 mL of ethyl acetate and filtered under vacuum with stirring for solid separation. The solid was washed with 20 mL of ethanol once, and dried under vacuum at 40° C. for 12 h to give 4.12 g off-white solid (62.14%), namely Compound (IV).

(2) Preparation of phenyl(4-((6,7-dimethoxyquinazolin-4-yl)oxy)phenyl)carbamate [Compound (VI)]

Phenyl chloroformate [Compound (V)] (1.64 g, 0.0105 mol) was slowly added to an ice-cooled solution of 4-((6,7-dimethoxyquinazolin-4-yl)oxy)aniline [Compound (IV)] (2.97 g, 0.01 mol) and potassium carbonate (1 g, 0.012 mol) in acetone (30 mL). After the addition, the water-water bath was removed. The reaction mixture was stirred at room temperature for 30 min, and added with methanol (20 mL). An inorganic salt solid was separated from the reaction solution, and the organic layer filtrate was concentrated and finally washed with ethyl acetate (10 mL) to give Compound (VI) in the form of a white powder (3.58 g, 85.85% yield).

(3) Preparation of multi-target kinase inhibitor [Compound (I-1)]

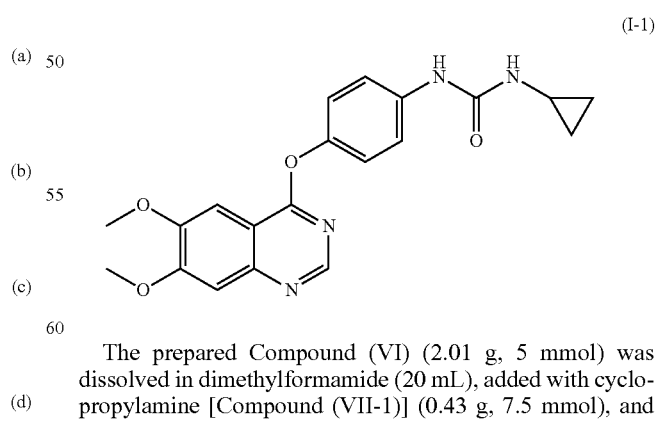

(I-1)

The prepared Compound (VI) (2.01 g, 5 mmol) was dissolved in dimethylformamide (20 mL), added with cyclopropylamine [Compound (VII-1)] (0.43 g, 7.5 mmol), and stirred at 80° C. for 2 h. Then the reaction mixture was cooled to 15-20° C., and poured into 50 mL of ice water. When the temperature was controlled to be 15-30° C., the resultant mixture was filtered under vacuum for solid separation. The solid was washed with water (20 mL) once, washed with acetonitrile (20 mL) once, and dried under vacuum to give the multi-target kinase inhibitor [Compound (I-1)] in the form of a powdery solid (1.25 g, 62.8% yield).

In the above preparation method, the structural formulas of the compounds are as follows:

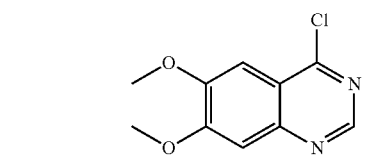
(II)

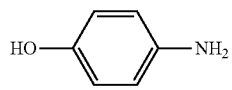
(III)

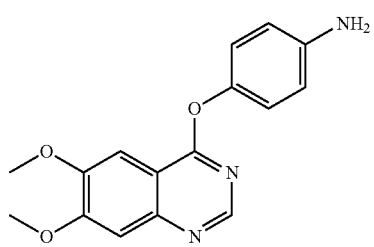
(IV)

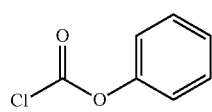
(V)

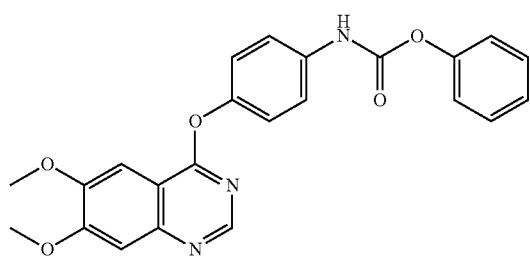
(VI)

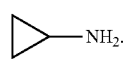
(VII-1)

In this example, the multi-target kinase inhibitor was further characterized by NMR spectroscopy and mass spectrometry, and the results are as follows: $^1$HNMR (400 MHz, DMSO-$d_6$): δ 8.52 (s, 1H), 8.39 (brs, 1H), 7.53 (s, 1H), 7.50 (m, 1H), 7.47 (m, 1H), 7.36 (s, 1H), 7.17 (m, 1H), 7.14 (m, 1H), 6.42 (d, J=2.6 Hz, 1H), 3.98 (s, 3H), 3.96 (s, 3H), 2.55 (m, 1H), 0.64 (m, 2H), 0.42 (m, 2H). ESI-MS (m/z): 381 [M+H]$^+$.

(4) Preparation of multi-target kinase inhibitor [Compound (I-2)]

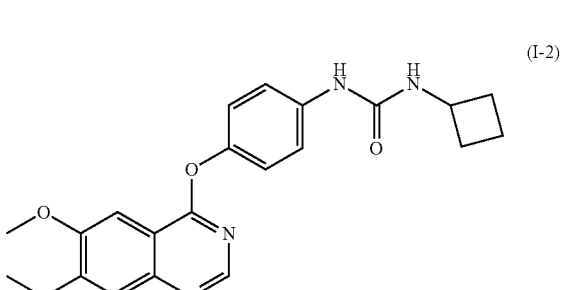
(I-2)

The prepared Compound (VI) (2.01 g, 5 mmol) was dissolved in dimethylformamide (20 mL), added with cyclobutylamine [Compound (VII-2)] (0.53 g, 7.5 mmol), and stirred at 80° C. for 2 h. Then the reaction mixture was cooled to 15-20° C., and poured into 50 mL of ice water. When the temperature was controlled to be 15-30° C., the resultant mixture was filtered under vacuum for solid separation. The solid was washed with water (20 mL) once, washed with acetonitrile (20 mL) once, and dried under vacuum to give the multi-target kinase inhibitor [Compound (I-2)] in the form of a powdery solid (1.38 g, 64.8% yield).

In the above preparation method, the structural formulas of the compounds are as follows:

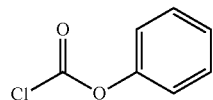
(V)

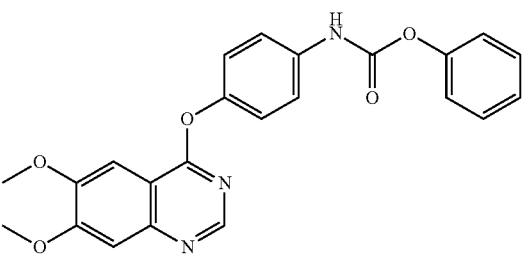
(VI)

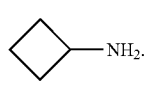
(VII-2)

In this example, the multi-target kinase inhibitor was further characterized by NMR spectroscopy and mass spectrometry, and the results are as follows: $^1$H NMR (400 MHz, DMSO-$d_6$): δ 8.50 (s, 1H), 8.37 (brs, 1H), 7.51 (s, 1H), 7.48 (m, 1H), 7.45 (m, 1H), 7.34 (s, 1H), 7.15 (m, 1H), 7.13 (m, 1H), 6.40 (d, J =2.6 Hz, 1H), 4.25 (m, 1H) 3.96 (s, 3H), 3.94 (s, 3H), 2.35 (m, 2H), 1.92 (m, 2H), δ 1.73 (m, 2H). ESI-MS (m/z): 395 [M+H]$^+$.

(5) Preparation of multi-target kinase inhibitor [Compound (I-3)]

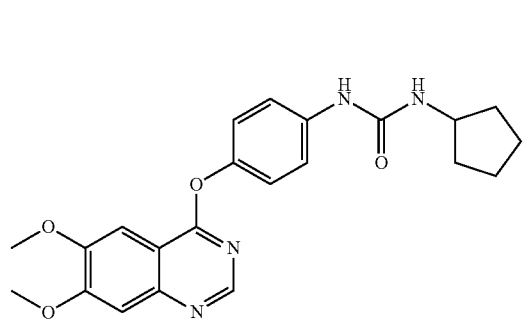

(I-3)

The prepared Compound (VI) (2.01 g, 5 mmol) was dissolved in dimethylformamide (20 mL), added with cyclopentylamine [Compound (VII-3)] (0.64 g, 7.5 mmol), and stirred at 80° C. for 2 h. Then the reaction mixture was cooled to 15-20° C., and poured into 50 mL of ice water. When the temperature was controlled to be 15-30° C., the resultant mixture was filtered under vacuum for solid separation. The solid was washed with water (20 mL) once, washed with acetonitrile (20 mL) once, and dried under vacuum to give the multi-target kinase inhibitor [Compound (I-3)] in the form of a powdery solid (1.19 g, 60.6% yield).

In the above preparation method, the structural formulas of the compounds are as follows:

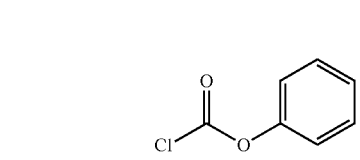

(V)

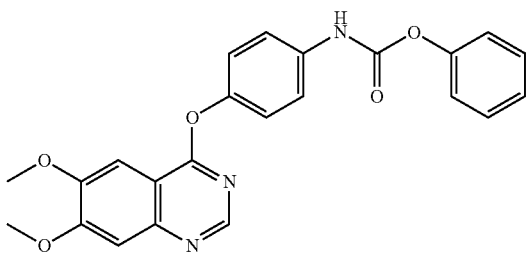

(VI)

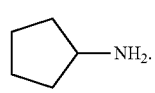

(VII-3)

In this example, the multi-target kinase inhibitor was further characterized by NMR spectroscopy and mass spectrometry, and the results are as follows: $^1$H NMR (400 MHz, DMSO-$d_6$): δ 8.59 (s, 1H), 8.44 (brs, 1H), 7.53 (s, 1H), 7.50 (m, 1H), 7.47 (m, 1H), 7.36 (s, 1H), 7.17 (m, 1H), 7.14 (m, 1H), 6.42 (d, J=2.6 Hz, 1H), 3.98 (s, 3H), 3.96 (s, 3H), 3.78 (m, 1H), 1.68 (m, 2H), 1.49 (m, 2H), 1.40 (m, 2H), 1.20 (m, 2H). ESI-MS (m/z): 409 [M+H]$^+$.

(6) Preparation of multi-target kinase inhibitor [Compound (I-4)]

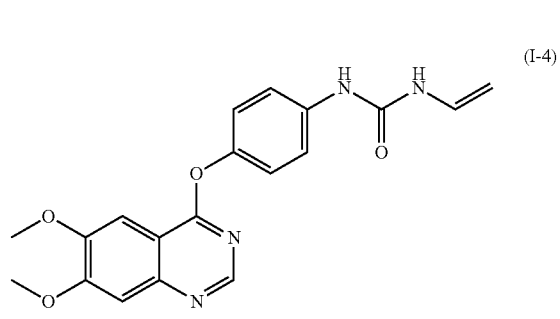 [SMILES: C=CNC(=O)Nc1ccc(Oc2ncnc3cc(OC)c(OC)cc23)cc1]

(I-4)

The prepared Compound (VI) (2.01 g, 5 mmol) was dissolved in dimethylformamide (20 mL), added with vinylamine [Compound (VII-4)] (0.32 g, 7.5 mmol), and stirred at 80° C. for 2 h. Then the reaction mixture was cooled to 15-20° C., and poured into 50 mL of ice water. When the temperature was controlled to be 15-30° C., the resultant mixture was filtered under vacuum for solid separation. The solid was washed with water (20 mL) once, washed with acetonitrile (20 mL) once, and dried under vacuum to give the multi-target kinase inhibitor [Compound (I)] in the form of a powdery solid (1.01 g, 58.8% yield).

In the above preparation method, the structural formulas of the compounds are as follows:

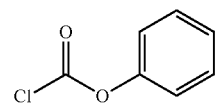

(V)

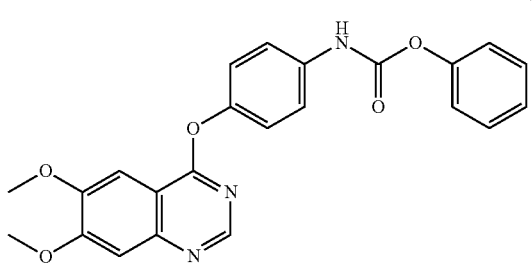

(VI)

(VII-4)

In this example, the multi-target kinase inhibitor was further characterized by NMR spectroscopy and mass spectrometry, and the results are as follows: $^1$H NMR (400 MHz, DMSO-$d_6$): δ 8.78 (s, 1H), 8.61 (brs, 1H), 7.41 (s, 1H), 7.50 (m, 1H), 7.47 (m, 1H), 7.31 (s, 1H), 7.18 (m, 1H), 7.15 (m, 1H), 6.42 (d, J=2.6 Hz, 1H), 6.05 (m, 1H), 5.61 (d, 1H), 4.04 (d, 1H), 3.98 (s, 3H), 3.96 (s, 3H). ESI-MS (m/z): 367 [M+H]$^+$.

(7) Preparation of multi-target kinase inhibitor [Compound (I-5)]

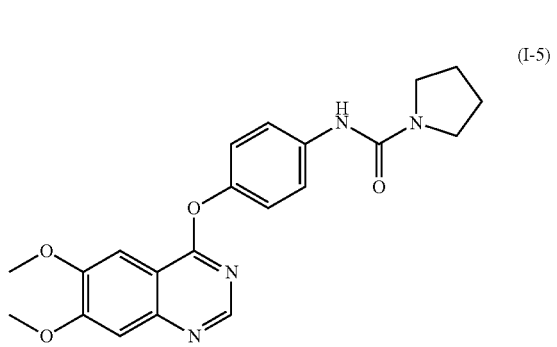 [SMILES: COc1cc2ncnc(Oc3ccc(NC(=O)N4CCCC4)cc3)c2cc1OC]

The prepared Compound (VI) (2.01 g, 5 mmol) was dissolved in dimethylformamide (20 mL), added with tetrahydropyrrole [Compound (VII-5)] (0.53 g, 7.5 mmol), and stirred at 80° C. for 2 h. Then the reaction mixture was cooled to 15-20° C., and poured into 50 mL of ice water. When the temperature was controlled to be 15-30° C., the resultant mixture was filtered under vacuum for solid separation. The solid was washed with water (20 mL) once, washed with acetonitrile (20 mL) once, and dried under vacuum to give the multi-target kinase inhibitor [Compound (I-5)] in the form of a powdery solid (1.26 g, 66.4% yield).

In the above preparation method, the structural formulas of the compounds are as follows:

(8) Preparation of multi-target kinase inhibitor [Compound (I-6)]

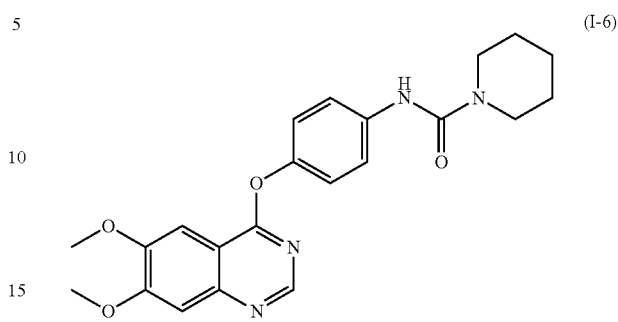

The prepared Compound (VI) (2.01 g, 5 mmol) was dissolved in dimethylformamide (20 mL), added with piperidine [Compound (VII-6)] (0.64 g, 7.5 mmol), and stirred at 80° C. for 2 h. Then the reaction mixture was cooled to 15-20° C., and poured into 50 mL of ice water. When the temperature was controlled to be 15-30° C., the resultant mixture was filtered under vacuum for solid separation. The solid was washed with water (20 mL) once, washed with acetonitrile (20 mL) once, and dried under vacuum to give the multi-target kinase inhibitor [Compound (I-6)] in the form of a powdery solid (1.27 g, 65.1% yield).

In the above preparation method, the structural formulas of the compounds are as follows:

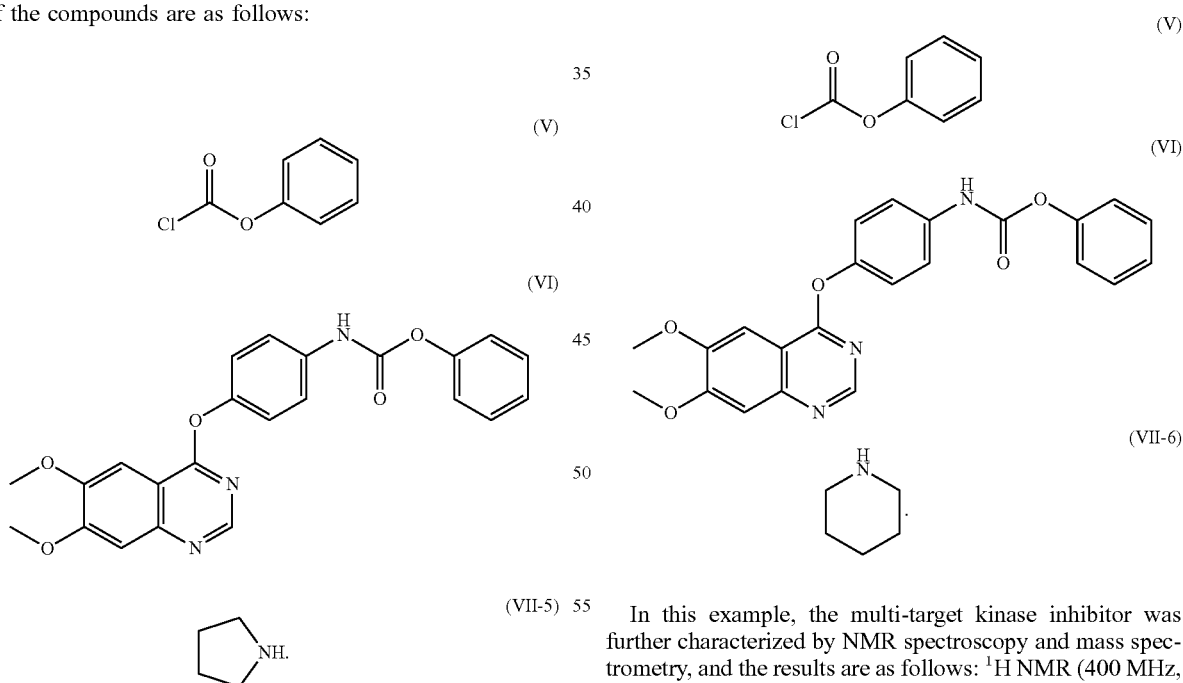

In this example, the multi-target kinase inhibitor was further characterized by NMR spectroscopy and mass spectrometry, and the results are as follows: $^1$H NMR (400 MHz, DMSO-$d_6$): δ 8.52 (s, 1H), 8.39 (brs, 1H), 7.53 (s, 1H), 7.50 (m, 1H), 7.47 (m, 1H), 7.36 (s, 1H), 7.17 (m, 1H), 6.42 (d, J=2.6 Hz, 1H), 3.98 (s, 3H), 3.96 (s, 3H), 3.25 (m, 4H), 1.70 (m, 4H). ESI-MS (m/z): 395 [M+H]$^+$.

In this example, the multi-target kinase inhibitor was further characterized by NMR spectroscopy and mass spectrometry, and the results are as follows: $^1$H NMR (400 MHz, DMSO-$d_6$): δ 8.53 (s, 1H), 8.40 (brs, 1H), 7.55 (s, 1H), 7.51 (m, 1H), 7.48 (m, 1H), 7.38 (s, 1H), 7.18 (m, 1H), 6.42 (d, J=2.6 Hz, 1H), 3.99 (s, 3H), 3.97 (s, 3H), 3.77 (m, 4H), 1.59 (m, 2H), 1.53 (m, 4H). ESI-MS (m/z): 409 [M+H]$^+$.

Example 2

In this example, the inhibitory activities of the multi-target kinase inhibitors described herein against RET, VEGFR3, and PDGFRA were investigated.

(I) Procedures

1. The compounds to be detected were accurately weighed and added into DMSO to form stock solutions, which were then diluted to desired concentrations with a buffer to give solutions of the compounds to be detected.
2. An RET or VEGFR3 or PDGFRA kinase solution, corresponding substrate solutions of Z'-LYTE, a buffer or a compound to be detected and ATP were added into a 384 reaction vessel, and reacted at room temperature for 1 h.
3. To each well was added a fluorescence enhancer, followed by incubation at room temperature for 1 h.
4. Data were read separately using a fluorescence analyzer.

(II) Data Processing

1. The relative inhibitory rate for each well was calculated according to a formula.
2. Active samples were diluted and tested for relative inhibitory rates, and the inhibitory rates $IC_{50}$ were calculated by plotting in the software Xlfit.

(III) Results

The experimental results are shown in Table 1:

TABLE 1

Inhibitory activities of multi-target kinase inhibitors against kinases RET, VEGFR3 and PDGFRA

| Compound | $IC_{50}$ (nM) | | | Experimental procedures |
|---|---|---|---|---|
| | RET | VEGFR3 | PDGFRA | |
| I-1 | 12 | 30 | 60 | Z'-LYTE |
| I-2 | 37 | 16 | 308 | Z'-LYTE |
| I-3 | 85 | 9 | 62 | Z'-LYTE |
| I-4 | 26 | 65 | 52 | Z'-LYTE |
| I-5 | 102 | 213 | 124 | Z'-LYTE |
| I-6 | 251 | 328 | 632 | Z'-LYTE |

Compounds with an ICso of less than 100 nM are considered capable of effectively inhibiting activities of target proteins. As can be seen from the experimental results in Table 1, the half-inhibitory concentrations of the multi-target kinase inhibitors provided herein against the targets are at nanomolar levels; the half-inhibitory concentrations of the multi-target kinase inhibitors (I-1), (I-3) and (I-4) against kinases RET, VEGFR3 and PDGFRA are all below 100 nM, and the half-inhibitory concentrations of the multi-target kinase inhibitor (I-2) against kinases RET and VEGFR3 are both below 100 nM. Therefore, the multi-target kinase inhibitors (I-1), (I-3) and (I-4) provided herein can effectively inhibit the enzymatic activities of RET, VEGFR3 and PDGFRA, and the multi-target kinase inhibitors (I-2) can effectively inhibit the enzymatic activities of RET and VEGFR3. It can be seen that the multi-target kinase inhibitors synthesized herein have most of the $IC_{50}$ within 100 nM, and are proved to have good druggability by in vitro experiments.

Example 3

In this example, the in vivo anti-tumor activity (liver cancer/esophageal cancer) of the multi-target kinase inhibitor [Compound (I-1)] was investigated according to the requirements in Guidelines for Pharmacodynamics of Antitumor Drugs. The experimental procedures and results are as follows:

(I) Experimental Procedures

Figure 2:
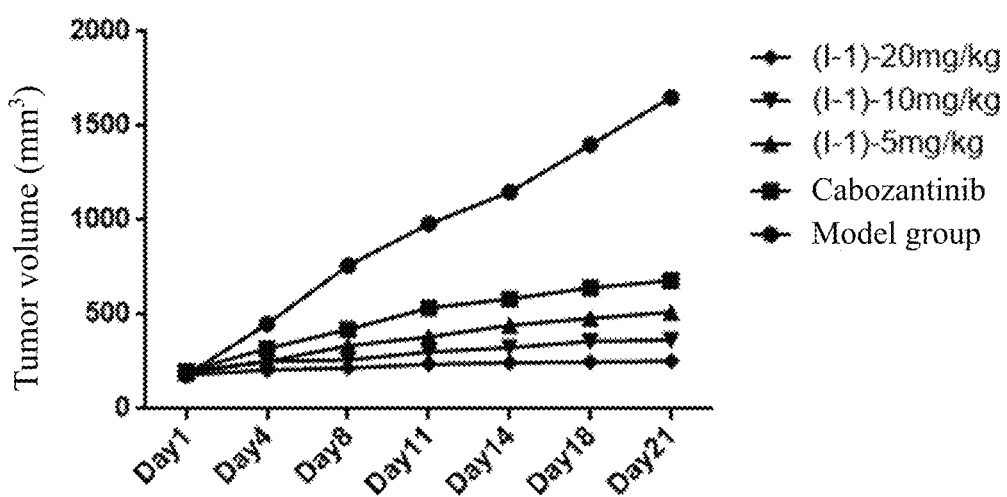
FIG. 2 shows the inhibition of tumor volumes in mice with KYSE 410 esophageal cancer by the multi-target kinase inhibitor [Compound (I-1)] of the present invention, wherein formula (I-1) represents Compound (I-1) of the multi-target kinase inhibitor of the present invention.

Tumor models of nude mice were established using SA/MC-7721 heptoma cells and KYSE 410 esophageal cancer cells that meet modeling conditions. The modeled mice were divided into 5 groups: a model group, a Compound (I-1) 5 mg/kg group, a Compound (I-1) 10 mg/kg group, a Compound (I-1) 20 mg/kg group, and a positive control group (sorafenib or cabozantinib). Administration was performed from the day of grouping that was counted as day 1 and for 21 consecutive days, and the 21st day was counted as day21. Tumor volumes were measured twice a week during the period of administration for statistical test. The test results are shown in FIG. 1 and FIG. 2.

(II) Results

Two groups of experiments for the tumor inhibitory effect of the multi-target kinase inhibitor [Compound (I-1)] on mice with SMMC-7721 liver cancer and mice with KYSE 410 esophageal cancer have similar test results, and the analysis of the results shows that: compared with the model group, the experimental groups at the dosages of 5 mg/kg, 10 mg/kg and 20 mg/kg and the positive control group presented lower tumor volumes; analysis of variance of the tumor volumes on day21 showed significant difference ($P<0.0001$), suggesting that Compound (I-1) provided herein has the same noticeable inhibitory effect on liver cancer as the positive control group does; compared with the positive control group, the experimental groups at the dosages of 10 mg/kg and 20 mg/kg presented lower tumor volumes, suggesting that Compound (I-1) provided herein has stronger in vivo anti-tumor activity than the positive drugs sorafenib and cabozantinib when at low dosage.

Example 4

In this example, the formulation and preparation process for tablets each containing 50 mg of the multi-target kinase inhibitor (I-1) are provided:

TABLE 2

Formulation for 1000 tablets containing multi-target kinase inhibitor (I-1)

| Component | Contents in weight percentages (%) | Content/Tablet (mg/Tablet) | Amount of prescription (g) |
|---|---|---|---|
| I-1 | 10.00 | 50.00 | 50.00 |
| Lactose | 75.00 | 375.00 | 375.00 |
| Polyvinyl-pyrrolidone | 5.00 | 25.00 | 25.00 |
| Low-substituted hydroxypropyl cellulose | 5.00 | 25.00 | 25.00 |
| Sodium croscarmellose | 3.00 | 15.00 | 15.00 |
| Silica | 1.00 | 5.00 | 5.00 |
| Magnesium stearate | 1.00 | 5.00 | 5.00 |
| Total | 100.00 | 500.00 | 500.00 (1000 tablets in total) |

The preparation process of the above tablets comprises the following steps.

1. The multi-target kinase inhibitor (I-1) was ultra-micronized and sieved with a sieve of more than 300 mesh to give a micronized powder starting material having a particle size $D_{90}$ controlled to be less than 50 μm, and the other excipients of the prescription were pre-treated by passing through a 60-mesh sieve; and 50 g of sieved multi-target kinase inhibitor starting material, 375 g of lactose, 25 g of polyvinylpyrrolidone, 25 g of low-substituted hydroxypropyl cellulose and 15 g of sodium croscarmellose were well mixed in a three-dimensional mixer to prepare a pre-mixed material.

2.5 g of magnesium stearate and 5 g of silica were added to the obtained pre-mixed material to give a mixed powder, the mixed powder was fully mixed in a three-dimensional mixer, the tablet weight range of tableting was determined according to the content results of the intermediate detection, and the mixture was tableted using a rotary tablet press to give the tablets.

Example 5

In this example, the formulation and preparation process for dispersible tablets each containing 50 mg of the multi-target kinase inhibitor (I-1) are provided:

TABLE 3

Formulation for 1000 dispersible tablets containing multi-target kinase inhibitor (I-1)

| Component | Contents in weight percentages (%) | Content/Tablet (mg/Tablet) | Amount of prescription (g) |
|---|---|---|---|
| I-1 | 10.00 | 50.00 | 50.00 |
| Microcrystalline cellulose | 17.50 | 87.50 | 87.50 |
| Lactose | 52.50 | 262.50 | 262.50 |
| Polyvinylpyrrolidone | 3.00 | 15.00 | 15.00 |
| Low-substituted hydroxypropyl cellulose | 10.00 | 50.00 | 50.00 |
| Sodium croscarmellose | 5.00 | 25.00 | 25.00 |
| Silica | 1.00 | 5.00 | 5.00 |
| Magnesium stearate | 1.00 | 5.00 | 5.00 |
| Total | 100.00 | 500.00 | 500.0 (1000 tablets in total) |

The preparation process of the above dispersible tablets comprises the following steps.

1. The multi-target kinase inhibitor (I-1) was ultra-micronized and sieved with a sieve of more than 300 mesh to give a micronized powder starting material having a particle size D90 controlled to be less than 50 μm, and the other excipients of the prescription were pre-treated by passing through a 60-mesh sieve; 50 g of sieved multi-target kinase inhibitor starting material, 87.5 g of microcrystalline cellulose, 262.5 g of lactose, 15 g of polyvinylpyrrolidone, 50 g of low-substituted hydroxypropyl cellulose and 25 g of sodium croscarmellose were well mixed in a three-dimensional mixer to give a pre-mixed material.

2.5 g of magnesium stearate and 5 g of silica were added to the obtained pre-mixed material to give a mixed powder, the mixed powder was fully mixed in a three-dimensional mixer, the tablet weight range of tableting was determined according to the content results of the intermediate detection, and the mixture was tableted using a rotary tablet press to give the dispersible tablets.

Example 6

In this example, the formulation and preparation process for dispersible tablets each containing 25 mg of the multi-target kinase inhibitor (I-1) are provided:

TABLE 4

Formulation for 1000 dispersible tablets containing multi-target kinase inhibitor (I-1)

| Component | Contents in weight percentages (%) | Content/Tablet (mg/Tablet) | Amount of prescription (g) |
|---|---|---|---|
| I-1 | 10.00 | 25.00 | 25.00 |
| Microcrystalline cellulose | 17.50 | 43.75 | 43.75 |
| Lactose | 52.50 | 131.25 | 131.25 |
| Polyvinylpyrrolidone | 3.00 | 7.50 | 7.50 |
| Low-substituted hydroxypropyl cellulose | 10.00 | 25.00 | 25.00 |
| Sodium croscarmellose | 5.00 | 12.50 | 12.50 |
| Silica | 1.00 | 2.50 | 2.50 |
| Magnesium stearate | 1.00 | 2.50 | 2.50 |
| Total | 100.00 | 250.00 | 250.00 (1000 tablets in total) |

The preparation process of the above dispersible tablets comprises the steps as in Example 5.

Example 7

In this example, the formulation and preparation process for dispersible tablets each containing 10 mg of the multi-target kinase inhibitor (I-1) are provided:

TABLE 5

Formulation for 1000 dispersible tablets containing multi-target kinase inhibitor (I-1)

| Component | Contents in weight percentages (%) | Content/Tablet (mg/Tablet) | Amount of prescription (g) |
|---|---|---|---|
| I-1 | 10.00 | 10.00 | 10.00 |
| Microcrystalline cellulose | 17.50 | 17.50 | 17.50 |
| Lactose | 52.50 | 52.50 | 52.50 |
| Polyvinylpyrrolidone | 3.00 | 3.00 | 3.00 |
| Low-substituted hydroxypropyl cellulose | 10.00 | 10.00 | 10.00 |
| Sodium croscarmellose | 5.00 | 5.00 | 5.00 |
| Silica | 1.00 | 1.00 | 1.00 |
| Magnesium stearate | 1.00 | 1.00 | 1.00 |
| Total | 100.00 | 100.00 | 100.00 (1000 tablets in total) |

The preparation process of the above dispersible tablets comprises the steps as in Example 5.

Example 8

In this example, the formulation and preparation process for dispersible tablets each containing 5 mg of the multi-target kinase inhibitor (I-1) are provided:

TABLE 6

Formulation for 1000 dispersible tablets containing multi-target kinase inhibitor (I-1)

| Component | Contents in weight percentages (%) | Content/Tablet (mg/Tablet) | Amount of prescription (g) |
|---|---|---|---|
| I-1 | 1.00 | 5.00 | 5.00 |
| Microcrystalline cellulose | 20.50 | 102.50 | 102.50 |
| Lactose | 58.50 | 292.50 | 292.50 |
| Polyvinyl-pyrrolidone | 3.00 | 15.00 | 15.00 |
| Low-substituted hydroxypropyl cellulose | 10.00 | 50.00 | 50.00 |
| Sodium croscarmellose | 5.00 | 25.00 | 25.00 |
| Silica | 1.00 | 5.00 | 5.00 |
| Magnesium stearate | 1.00 | 5.00 | 5.00 |
| Total | 100.00 | 500.00 | 500.00 (1000 tablets in total) |

The preparation process of the above dispersible tablets comprises the steps as in Example 5.

Example 9

In this example, the formulation and preparation process for sustained-release tablets each containing 250 mg of the multi-target kinase inhibitor (I-1) are provided:

TABLE 7

Formulation for 1000 sustained-release tablets containing multi-target kinase inhibitor (I-1)

| Component | Contents in weight percentages (%) | Content/Tablet (mg/Tablet) | Amount of prescription (g) |
|---|---|---|---|
| I-1 | 50.00 | 250.00 | 250.00 |
| Hydroxypropyl methylcellulose | 17.50 | 87.50 | 87.50 |
| Sodium alginate | 22.50 | 112.50 | 112.50 |
| Polyvinyl-pyrrolidone | 3.00 | 15.00 | 15.00 |
| Sodium croscarmellose | 5.00 | 25.00 | 25.00 |
| Silica | 1.00 | 5.00 | 5.00 |
| Magnesium stearate | 1.00 | 5.00 | 5.00 |
| Total | 100.00 | 500.00 | 500.00 (1000 tablets in total) |

The preparation process of the above dispersible tablets comprises the following steps.

1. The multi-target kinase inhibitor (I-1) was ultra-micronized and sieved with a sieve of more than 300 mesh to give a micronized powder starting material having a particle size $D_{90}$ controlled to be less than 50 μm, and the other excipients of the prescription were pre-treated by passing through a 60-mesh sieve; and 250 g of sieved multi-target kinase inhibitor (I-1), 87.5 g of hydroxypropyl methylcellulose, 112.5 g of sodium alginate, and 15 g of polyvinylpyrrolidone were well mixed in a high-efficiency mixing granulator, and added with a 30% aqueous solution of ethanol to give a soft material, the soft material was dried and granulated, and added with 25 g of sodium croscarmellose, and then the resulting mixture was well mixed in a three-dimensional mixer to give a pre-mixed material.

2.5 g of magnesium stearate and 5 g of silica were added to the obtained pre-mixed material to give a mixed powder, the mixed powder was fully mixed in a three-dimensional mixer, the tablet weight range of tableting was determined according to the content results of the intermediate detection, and the mixture was tableted using a rotary tablet press to give the sustained-release tablets containing the multi-target kinase inhibitor.

Example 10

In this example, the formulation and preparation process for capsules each containing 50 mg of the multi-target kinase inhibitor (I-1) are provided:

TABLE 8

Formulation for 1000 capsules containing multi-target kinase inhibitor (I-1)

| Component | Contents in weight percentages (%) | Content/Tablet (mg/Tablet) | Amount of prescription (g) |
|---|---|---|---|
| I-1 | 20.00 | 50.00 | 50.00 |
| Microcrystalline cellulose | 67.00 | 167.50 | 167.50 |
| Lactose | 10.45 | 26.00 | 26.00 |
| Silica | 1.50 | 3.75 | 3.75 |
| Magnesium stearate | 1.00 | 2.50 | 2.50 |
| Sodium dodecyl sulfate | 0.05 | 0.25 | 0.25 |
| Total | 100.00 | 250.00 | 250.00 (1000 capsules in total) |

The preparation process of the above capsules comprises the following steps.

1. The multi-target kinase inhibitor (I-1) was ultra-micronized and sieved with a sieve of more than 300 mesh to give a micronized powder starting material having a particle size $D_{90}$ controlled to be less than 50 μm, and the other excipients of the prescription were pre-treated by passing through a 60-mesh sieve; 50 g of sieved multi-target kinase inhibitor starting material, 167.5 g of microcrystalline cellulose, and 26 g of lactose were well mixed in a three-dimensional mixer to give a pre-mixed material.

2. 2.5 g of magnesium stearate and 3.75 g of silica were added to the obtained pre-mixed material to give a mixed powder, the mixed powder was fully mixed in a three-dimensional mixer, the filling amount weight range was determined according to the content results of the intermediate detection, and capsules were filled using an automatic capsule filler to give the capsules containing the multi-target kinase inhibitor.

Example 11

In this example, the formulation and preparation process for granules each containing 50 mg of the multi-target kinase inhibitor (I-1) are provided:

TABLE 9

Formulation for 1000 pouches of granules containing multi-target kinase inhibitor (I-1)

| Component | Contents in weight percentages (%) | Amount/Pouch (mg/Pouch) | Amount of prescription (g) |
|---|---|---|---|
| I-1 | 10.00 | 50.00 | 50.00 |
| Sucrose | 67.20 | 336.00 | 336.00 |

TABLE 9-continued

Formulation for 1000 pouches of granules
containing multi-target kinase inhibitor (I-1)

| Component | Contents in weight percentages (%) | Amount/Pouch (mg/Pouch) | Amount of prescription (g) |
|---|---|---|---|
| Gum arabic | 5.00 | 25.00 | 25.00 |
| Tragacanth | 10.00 | 50.00 | 50.00 |
| Low-substituted hydroxypropyl cellulose | 5.00 | 25.00 | 25.00 |
| Silica | 1.50 | 7.50 | 7.50 |
| Magnesium stearate | 1.00 | 5.00 | 5.00 |
| Vanillin | 0.10 | 0.50 | 0.50 |
| Orange powdery essence | 0.20 | 1.00 | 1.00 |
| Total | 100.00 | 500.00 | 500.00 (1000 pouches in total) |

The preparation process of the above granules comprises the following steps.

1. The multi-target kinase inhibitor (I-1) was ultra-micronized and sieved with a sieve of more than 300 mesh to give the multi-target kinase inhibitor (I-1) having a particle size $D_{90}$ controlled to be less than 50 μm, and the other excipients of the prescription were pre-treated by passing through a 60-mesh sieve.

2. The sieved multi-target kinase inhibitor (I-1), sucrose, gum arabic and tragacanth were well mixed in a high-efficiency mixing granulator, added with a proper amount of a 30% ethanol solution and well mixed to give a soft material, the soft material was granulated by passing through a 30-mesh sieve, the sieved soft material was dried in a fluidized bed at 50-60° C., and the dried material was sieved with a 30-mesh sieve to give dry granules.

3. A lubricating glidant and a flavoring agent were added to the dry granules to give a mixed powder, and the mixed powder was well mixed in a multi-directional motion mixer, and packaged by using a granule packer to give the granules containing the multi-target kinase inhibitor.

Efficacy Example 1

100 tablets of each sample prepared in Examples 4 and 5 were investigated in vitro for dissolution rates in various dissolution media.

Figure 3:
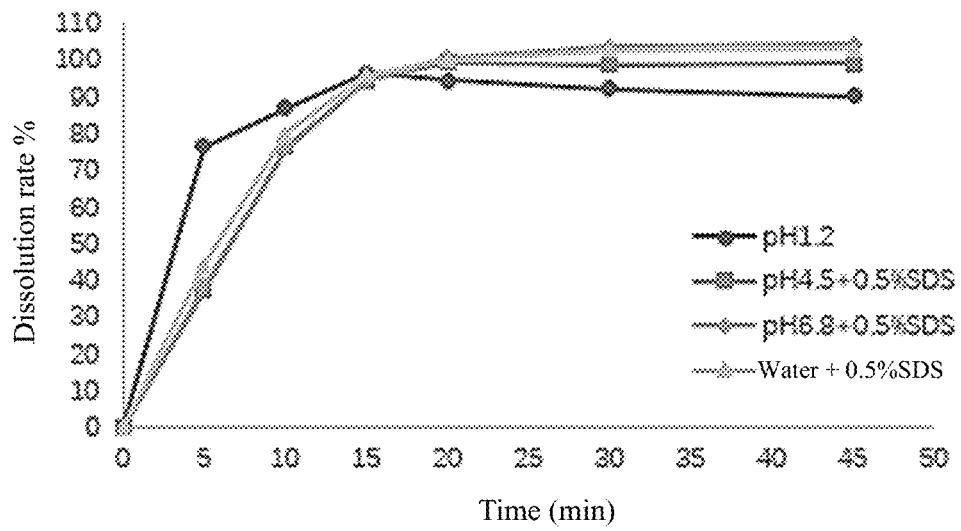
FIG. 3 shows the dissolution rates of the pharmaceutical composition samples of Example 4 of the present invention in dissolution media with different pH values.
Figure 4:
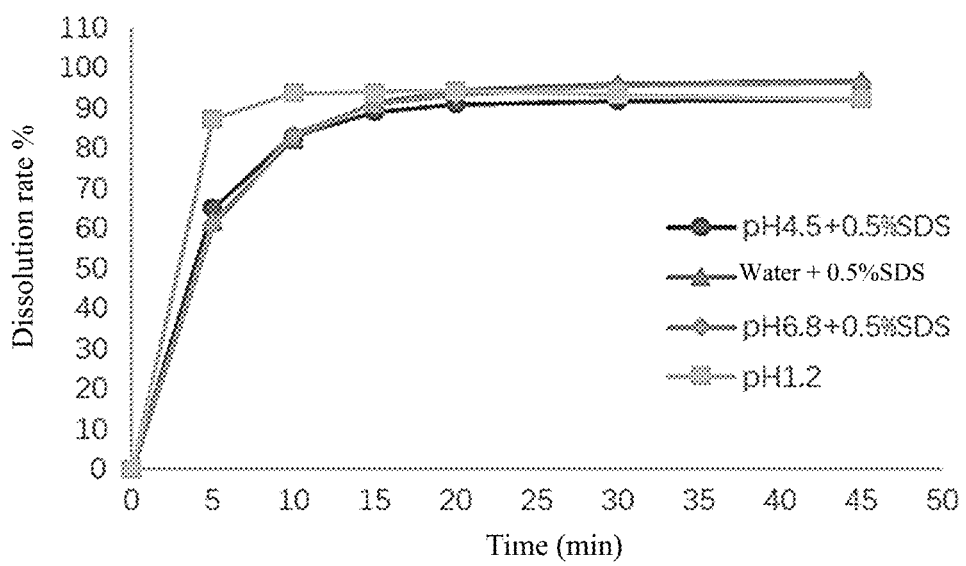
FIG. 4 shows the dissolution rates of the pharmaceutical composition samples of Example 5 of the present invention in dissolution media with different pH values.

Dissolution tests were performed according to the content homogeneity inspection method of Chapter 0931 in Chinese Pharmacopoeia (Volume IV, 2015 Edition), and the second method was adopted. The volume of a dissolution medium is 900 mL, and the rotating speed is 50 rpm. Purified water, a hydrochloric acid solution with a pH of 1.2, an acetate buffer with a pH of 4.5 and a phosphate buffer with a pH of 6.8 were adopted as the dissolution media, in which except for the hydrochloric acid solution with a pH of 1.2, the other three dissolution media were all added with a 0.5% sodium dodecyl sulfate (abbreviated as "SDS") surfactant. Dissolution rates of the samples of Examples 4 and 5 in 4 dissolution media were measured by HPLC, and the dissolution data recorded are shown in Table 10, Table 11, FIG. 3 and FIG. 4:

TABLE 10

Dissolution rates of the samples of Example 4 in dissolution media with different pH values

| Medium | Time | | | | | |
|---|---|---|---|---|---|---|
| | 5 min | 10 min | 15 min | 20 min | 30 min | 45 min |
| pH1.2 | 76.35 | 86.73 | 96.34 | 94.31 | 92.11 | 90.21 |
| pH4.5 + 0.5% SDS | 37.40 | 76.52 | 94.36 | 99.10 | 98.57 | 98.95 |
| pH6.8 + 0.5% SDS | 38.48 | 75.74 | 94.41 | 100.68 | 103.58 | 104.02 |
| Water + 0.5% SDS | 44.19 | 80.15 | 95.89 | 100.05 | 102.35 | 102.69 |

TABLE 11

Dissolution rates of the samples of Example 5 in dissolution media with different pH values

| Medium | Time | | | | | |
|---|---|---|---|---|---|---|
| | 5 min | 10 min | 15 min | 20 min | 30 min | 45 min |
| pH1.2 | 87.17 | 93.66 | 93.90 | 94.26 | 93.26 | 92.18 |
| pH4.5 + 0.5% SDS | 64.99 | 82.96 | 88.94 | 90.84 | 91.74 | 92.14 |
| pH6.8 + 0.5% SDS | 60.70 | 83.22 | 90.87 | 93.34 | 95.63 | 96.20 |
| Water + 0.5% SDS | 61.58 | 82.11 | 91.09 | 94.20 | 96.09 | 96.70 |

Two groups of multi-target kinase inhibitor samples of Example 4 and Example 5 were investigated in vitro for dissolution rates in various dissolution media, and the results show that the sample of Example 4 had in vitro dissolution rates of no less than 94 in different dissolution media at minute 15, and the sample of Example 5 had in vitro dissolution rates of no less than 88 in different dissolution media at minute 15, indicating that the pharmaceutical composition of the present invention dissolves quickly when prepared into tablets, and the drug release can reach a plateau at minute 15. The results also show downward trends in the dissolution rates of the pharmaceutical composition samples with increasing pH values, and on the other hand, the samples in the forms of a common tablet or dispersible tablet of oral solid preparations are expected to be dissolved in the stomach and absorbed through the upper half of the small intestine of a patient, indicating that the pharmaceutical compositions of the present invention are improved in dissolution rates and in vivo absorption when prepared into tablets by a certain production process. In addition, according to the content of the multi-target kinase inhibitor contained in the pharmaceutical composition as an active ingredient, the pharmaceutical composition only needs to be orally taken once a day by a patient, which greatly improves the compliance of the patient.

Finally, it should be noted that the above examples are only for illustrating the technical solution of the present invention and not for limiting the protection scope of the present invention, and although the present invention is described in detail with reference to the preferred embodiments, it will be understood by those skilled in the art that modifications or equivalent substitutions can be made to the technical solution of the present invention without departing from the spirit and scope of the technical solution of the present invention.

The invention claimed is:

1. A compound represented by formula (I) or a pharmaceutically acceptable salt thereof

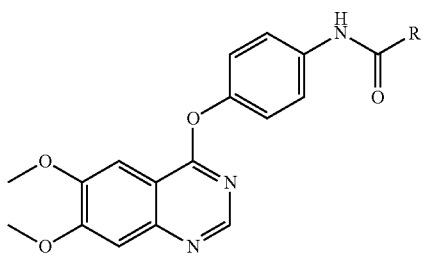

wherein R is formula (a):

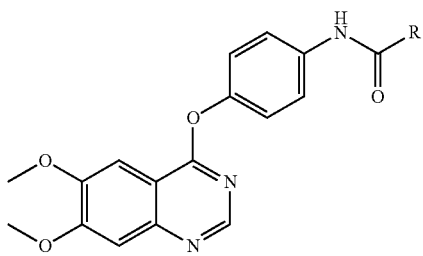

2. A method for preparing the compound or the pharmaceutically acceptable salt thereof according to claim 1, comprising:
   (1) reacting a compound of formula (II) with a compound of formula (III) to prepare a compound of formula (IV);
   (2) reacting a compound of formula (IV) with a compound of formula (V) to prepare a compound of formula (VI); and
   (3) reacting a compound of formula (VI) with a compound of formula (VII) to prepare the compound of formula (I);
   the structural formulas of formula (II), formula (III), formula (IV), formula (V), formula (VI) and formula (VII) being shown as follows:

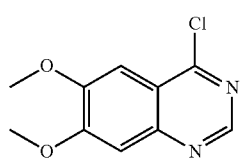

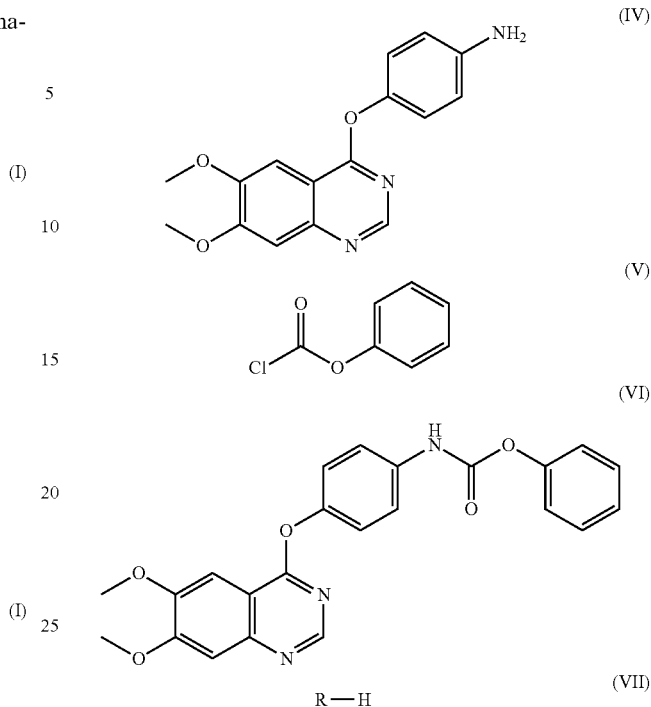

wherein R is formula (a).

3. A method for treating diseases caused by abnormal signal transduction pathways of RET, VEGFR3 and PDGFRA, comprising administering an effective amount of a composition to a subject in need thereof, wherein the composition comprises the compound or the pharmaceutically acceptable salt thereof according to claim 1.

4. The method according to claim 3, wherein the diseases caused by abnormal signal transduction pathways of RET, VEGFR3 and PDGFRA are cancers; the cancers are at least one of liver cancer, breast cancer, lung cancer, colorectal cancer, brain cancer, ovarian cancer, uterine tumor, prostate cancer, kidney cancer, melanoma, head and neck cancer, sarcoma, lymphoma and leukemia.

5. The compound or the pharmaceutically acceptable salt thereof according to claim 1, wherein the pharmaceutically acceptable salt is a salt formed from the compound and an acid; the acid is methanesulfonic acid, hydrochloric acid, acetic acid, trifluoroacetic acid, tartaric acid, malic acid, citric acid, hydrobromic acid, phosphoric acid, sulfuric acid, trifluoromethanesulfonic acid, benzenesulfonic acid, p-toluenesulfonic acid, 1-naphthalenesulfonic acid, 2-naphthalenesulfonic acid, lactic acid, oxalic acid, succinic acid, fumaric acid, maleic acid, salicylic acid, benzoic acid, phenylacetic acid or mandelic acid.

6. A pharmaceutical composition, comprising the compound or the pharmaceutically acceptable salt thereof according to claim 1 as an active ingredient.

7. The pharmaceutical composition according to claim 6, further comprising at least one pharmaceutical excipient known in the pharmaceutical art, wherein the pharmaceutical excipient includes one or more of a filler, a binder, a disintegrant, and a lubricating glidant.

8. The pharmaceutical composition according to claim 6, wherein the compound or the pharmaceutically acceptable salt thereof accounts for 1-50 wt % of the pharmaceutical composition.

9. The pharmaceutical composition according to claim 7, wherein the pharmaceutical excipient comprises 10-80 wt % of a filler, 1-45 wt % of a binder, 5-20 wt % of a disintegrant and 0.1-10 wt % of a lubricating glidant, based on the pharmaceutical composition.

10. The pharmaceutical composition according to claim 7, wherein the filler is selected from at least one of lactose, microcrystalline cellulose, mannitol, sorbitol, calcium hydrogen phosphate, starch, pregelatinized starch, chitosan, sucrose, starch hydrolyzed oligosaccharides, and silicified microcrystalline cellulose; the binder is selected from at least one of hydroxypropyl methylcellulose, dextrin, carbomer, xanthan gum, gum arabic, sodium alginate, tragacanth, maltodextrin, polyvinylpyrrolidone, and hydroxypropyl cellulose; the disintegrant is selected from at least one of low-substituted hydroxypropyl cellulose, crospovidone, sodium croscarmellose, cross-linked sodium carboxymethyl starch and sodium carboxymethyl starch; the lubricating glidant is selected from at least one of magnesium stearate, calcium stearate, stearic acid, sodium fumarate, sodium dodecyl sulfate, glyceryl behenate, talc, silica, polyethylene glycol and sodium stearyl fumarate.

11. The pharmaceutical composition according to claim 6, wherein the pharmaceutical composition can be prepared in any pharmaceutically acceptable dosage form.

12. The pharmaceutical composition according to claim 11, wherein the dosage form is an oral solid preparation.

\* \* \* \* \*